United States Patent

El-Hanany et al.

[11] Patent Number: 4,701,607
[45] Date of Patent: Oct. 20, 1987

[54] TEMPERATURE CONTROL LASER DETECTION APPARATUS

[75] Inventors: Uri El-Hanany; Uri Lachish, both of Rehovot; Shlomo Rotter, Rishon Le-Zion; Eli Adler, Holon, all of Israel

[73] Assignees: Arel Control Systems, Ltd.; State of Israel, both of Yavne, Israel

[21] Appl. No.: 723,580

[22] Filed: Apr. 15, 1985

[51] Int. Cl.[4] .......................... G01J 1/00; H01S 3/13
[52] U.S. Cl. .................................. 250/205; 356/319; 372/32; 372/34
[58] Field of Search ..................... 250/205; 356/319; 372/29, 33, 34, 35, 36, 31, 32, 25

[56] References Cited

U.S. PATENT DOCUMENTS 3,858,056 12/1974 Melamed et al. ............... 372/34 X
4,410,273 10/1983 Mantz et al. ....................... 356/319

Primary Examiner—Eugene R. LaRoche
Assistant Examiner—James C. Lee
Attorney, Agent, or Firm—John H. Lynn

[57] ABSTRACT

Laser detection apparatus comprising a laser defining an active region and providing a double beam of coherent radiation, a sample to be tested located in a first part of the double beam of coherent radiation, a radiation detector arranged to receive radiation passing through the sample to be tested for providing an output indication of absorbance, a reference sample disposed in a second part of the double beam, apparatus for sensing absorption of the coherent radiation at the reference sample, apparatus for providing selectable heating of the active region of the laser, and apparatus for providing a control signal to the selectable heating apparatus in accordance with the sensed absorption of the coherent radiation at the reference sample.

4 Claims, 4 Drawing Figures

TEMPERATURE CONTROL LASER DETECTION APPARATUS

FIELD OF THE INVENTION

The present invention relates to lasers generally and more particularly to temperature stabilization of injection lasers.

BACKGROUND OF THE INVENTION

Injection lasers include a wide variety of lasers. Most of these are of the Gallium-Arsenide family and are currently not used for spectroscopic purposes. There are also known other injection lasers, such as lasers of the lead-salt family, including (Pb,Sn)Te, which are currently used for spectroscopic applications. Lasers of this type are commonly termed, tunable diode lasers.

It is well known that the resonance frequency of tunable diode lasers is dependent on the temperature of the active region of the laser. The maintenance of a predetermined resonance frequency to high precision over time is of significance when the laser is being used for spectroscopic examinations.

Laser spectroscopes are known for performing very high accuracy spectroscopic measurements to the order of $10^{-4}$ cm$^{-1}$. These systms which are commercially available from Laser Analytics, of Bedford, Mass., U.S.A., normally comprise a laser which radiates through a sample gas onto a detector, which provides an output indication of the absorption of the laser radiation at the precise radiation frequency.

The accuracy of these measurements is limited by the temperature stability of the laser head which is usually maintained by using a temperature sensor such as a silicon diode and appropriate electronic apparatus.

In order to overcome the problem of frequency stabilization, a current feedback arrangement has been used by a number of investigators. See I. I. Zasavitskii et al, "Temperature Regulation Of A Tunable Diode Laser Within (about) 10 −5 K", Soviet Tech. Phys. Lett. Vol 8(10), October, 1982 pp. 502, 503. In this arrangement, the laser beam is split into two branches, one of which passes through a measurement cell and one of which passes through a cell containing a reference gas and impinges on a detector which measures the absorbed radiation.

An absorption line shape of the reference gas is obtained directly by modulating the electric current operating the laser, thus modulating the laser radiation frequency around the central frequency of the absorption line. This line shape is detected by special apparatus which operative to control the bias current of the laser via a current feedback mechanism. Thus any line shift evolving in the system as a result of a temperature fluctuation induces a current of opposite effect which pushes the line center back to its predetermined place. Thus the laser central frequency is locked to the center of the absorption line.

There are some significant disadvantages to the current feedback approach to laser frequency stabilization in which temperature fluctuations are compensated by current fluctuations, since current fluctuations induce inherent radiation intensity instability in the laser. Furthermore, the laser radiation is modulated at a whole predetermined range around the frequency of the center absorption line, but only this center frequency is stabilized while the side band radiation can still fluctuate in both frequency and intensity according to the current/frequency/temperature interrelationship.

There has also been proposed by H. Tsuchida et al in an article entitled "Frequency Stability Measurement of Feedback Stabilized AIGaAs DH Laser" in *Journal of Applied Physics*, Vol. 19, No. 12, December, 1980, pp. 1721–1724, a technique whereby a thermal module associated with the laser is controlled by an output signal produced by a feedback arrangement incorporating a Fabry-Perot interferometer.

In this arrangement, the laser operates under conditions of constant current and constant temperature, thus eliminating the disadvantages of current feedback described hereinabove. However, the Fabry-Perot fringes which are used for locking the radiation frequency of the laser are much broader than absorption lines of gases in most cases. Therefore, the degree of stabilization that can be achieved with this apparatus is lower than that which can be achieved using gas absorption lines as the active feedback parameters. Furthermore, the Fabry-Perot interferometer is itself sensitive to temperature and atmospheric pressure in its immediate environment thus adding additional instability factors.

SUMMARY OF THE INVENTION

The present invention seeks to provide a highly stable laser spectrographic device which is useful with samples at relatively low concentrations and which is relatively inexpensive and simple in construction.

There is thus provided in accordance with a preferred embodiment of the present invention laser detection apparatus comprising a laser defining an active region and providing a double beam of coherent radiation, a sample to be tested located in a first part of the double beam of coherent radiation, a radiation detector arranged to receive radiation passing through the sample to be tested for providing an output indication of absorbance, a reference sample disposed in a second part of the double beam, apparatus for sensing absorption of the coherent radiation at the reference sample, apparatus for providing selectable heating of the active region of the laser, and apparatus for providing a control signal to the selectable heating apparatus in accordance with the sensed absorption of the coherent radiation at the reference sample.

Further in accordance with a preferred embodiment of the invention, the apparatus for providing selectable heating of the active region of the laser comprises a resistor.

BRIEF DESCRIPTION OF THE DRAWINGS

The present invention will be understood and appreciated more fully from the following detailed description taken in conjunction with the drawings in which.

DETAILED DESCRIPTION OF THE PREFERRED EMBODIMENT

Figure 1:
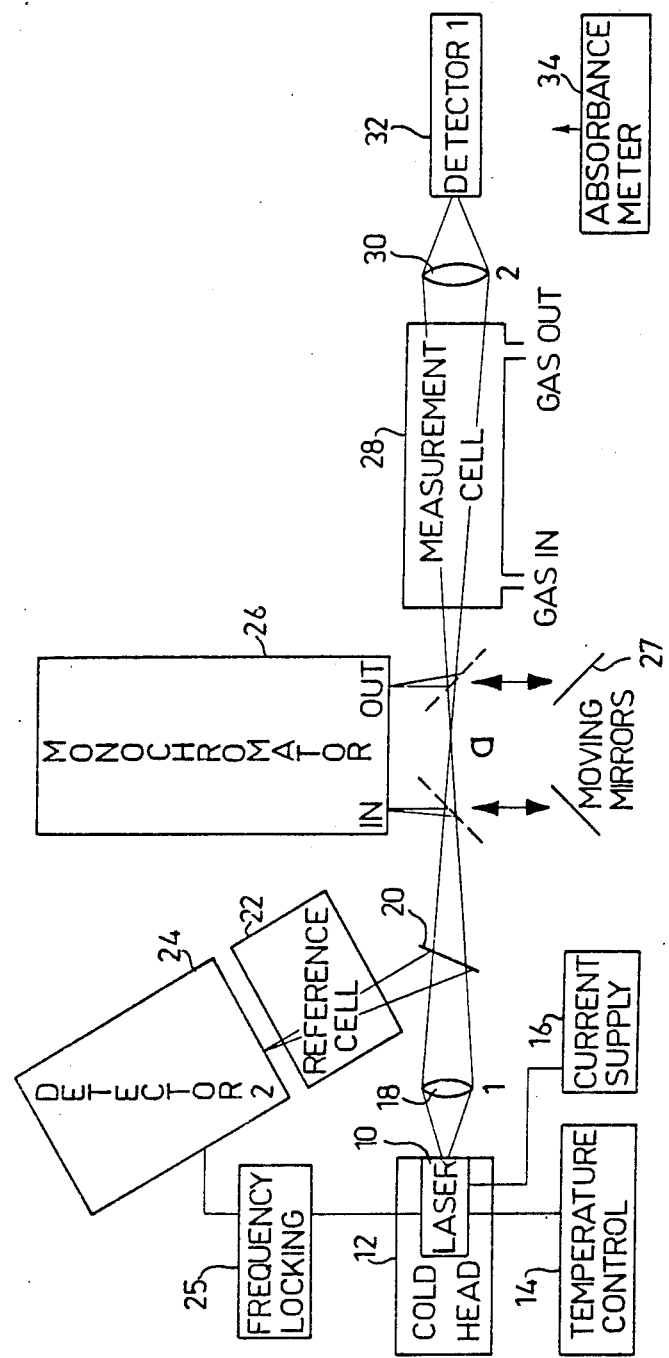
FIG. 1 is a block diagram illustration of the laser measurement device constructed and operative in accordance with a preferred embodiment of the invention.

Reference is now made to FIG. 1 which illustrates laser measurement apparatus constructed and operative in accordance with a preferred embodiment of the present invention. The apparatus of FIG. 1 comprises an injection laser 10, such as a tunable diode laser, mounted on the cold stage of a cryostat 12. Laser 10 is supplied with temperature control means 14 and with a current supply 16. The coherent radiation output of the laser, which is a modulated monochromatic output is supplied via a focussing lens 18 in a focussed radiation beam.

The focussed radiation beam impinges first on a partially reflecting mirror 20, on conventional construction, which reflects part of the radiation and directs it onto a cell 22 containing a reference material, typically a gas, of precisely known spectral properties. The radiation, having passed through cell 22, then impinges on a detector 24 which measures the radiation transmitted through the gas in cell 22.

The output of detector 24 supplies an absorption line shape signal to feedback control apparatus 25 for maintaining the precise frequency output of the laser 10. It is appreciated that detector 24 and feedback control 25 operate in a feedback mode such that a variation of the frequency of the radiation output of the laser 10 is sensed by the detector 24 as a shift of the absorption line from its predetermined position which causes feedback control 25 to increase or decrease the temperature at the active region of the laser 10 in order to produce the required frequency stability.

Downstream of mirror 20 the laser radiation output is supplied to a measurement cell 28 which contains a sample gas to be tested and is provided with a suitable gas inlet and outlet, as required. The radiation beam, after having passed through measurement cell 28, is focussed by a lens 30 onto a detector 32 which measures the laser radiation transmitted through the sample cell. The output of detector 32 is fed to a specially designed absorbance meter 34 which is capable of detection and measurement of weak absorption signals by means of signal averaging.

Figure 3:
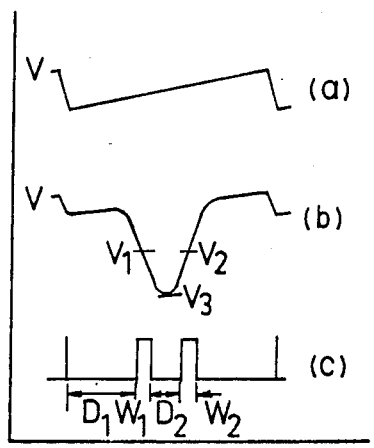
FIG. 3 is a timing diagram illustrating the data acquisition of the absorption signal in the apparatus of the invention.

The operation of the absorbance meter is best understood from a consideration of FIGS. 3A-3C. FIG. 3B illustrates a typical intensity signal of absorption line shape obtained by frequency modulation of the laser radiation as shown in FIG. 3A. FIG. 3C illustrates a series of consecutive time intervals ($D_1, W_1, D_2, W_2$) adjusted in such a way that the intervals $W_1$ and $W_2$ overlap the two corresponding slopes of the absorption line and the time interval $D_2$ overlaps the peak of the absorption line.

The signal intensities $V_1$ and $V_2$ and $V_3$ represent the respective averages taken by means of commercial sample-and-hold integrated chips during the time intervals $W_1$, $W_2$ and $D_2$. The difference between $V_3$ and the average of $V_1$ and $V_2$ is read out as an absorption signal.

Figure 2:
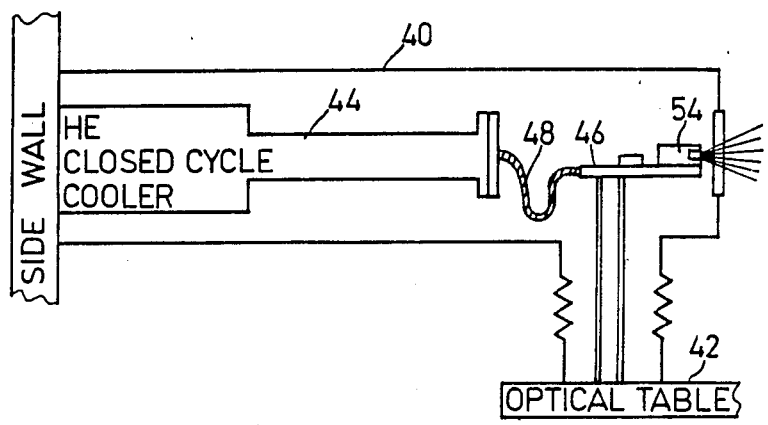
FIG. 2 is a detailed illustration of the laser portion of the apparatus of FIG. 1.
Figure 2:
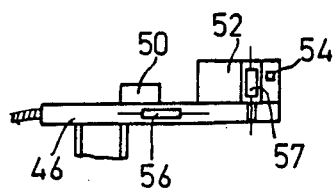

Reference is now made to FIG. 2 which illustrates the arrangement of the laser in greater detail. It is seen that there is provided a sealed enclosure 40, which is preferably mounted to a side wall of a housing or other element which is vibrationally decoupled from the optical table on which the spectrometer is mounted. Disposed within the sealed enclosure is a cryogenic unit 44, such as a Helium closed cycle cooler which provides heat sinking for a laser mounting base 46 via a copper braid 48.

A base 46, mounted onto an optical table, supports a silicon diode 50, and a laser holder 52, which in turn supports the injection laser 54. Base 46 and laser holder 52 are typically formed of copper.

The temperature of base 46 is maintained at a predetermined level by means of a heating element 56 and a silicon diode temperature sensor 50 connected to an electronic temperature control unit 14. This circuit provides coarse temperature tuning of the base and laser holder.

According to a preferred embodiment of the present invention, heating means 57 in the form of a resistor, is embedded in laser holder 52 for providing precisely controllable heating of laser 54 in response to control signals received from the reference feedback arrangement described above, for providing precise frequency control of the coherent radiation output of the laser.

The operation of the feedback control apparatus is best understood from a consideration of FIGS. 3A-3C and 4. FIG. 3B illustrates a typical intensity signal of absorption line shape obtained by frequency modulation of the laser radiation as shown in FIG. 3A. FIG. 3C illustrates a series of consecutive time intervals ($D_1, W_1, D_2, W_2$) adjusted in such a way that the intervals $W_1$ and $W_2$ overlap the two corresponding slopes of the absorption line.

A right shift of the absorption line, relative to the intervals $W_1$ and $W_2$ has the effect that the average signal intensity $V_1$ during the interval $W_1$ increases. On the other hand, the average signal intensity $V_2$ during interval $W_2$, decreases. A left shift of the absorption line effects changes of $V_1$ and $V_2$ in opposite directions.

Figure 4:
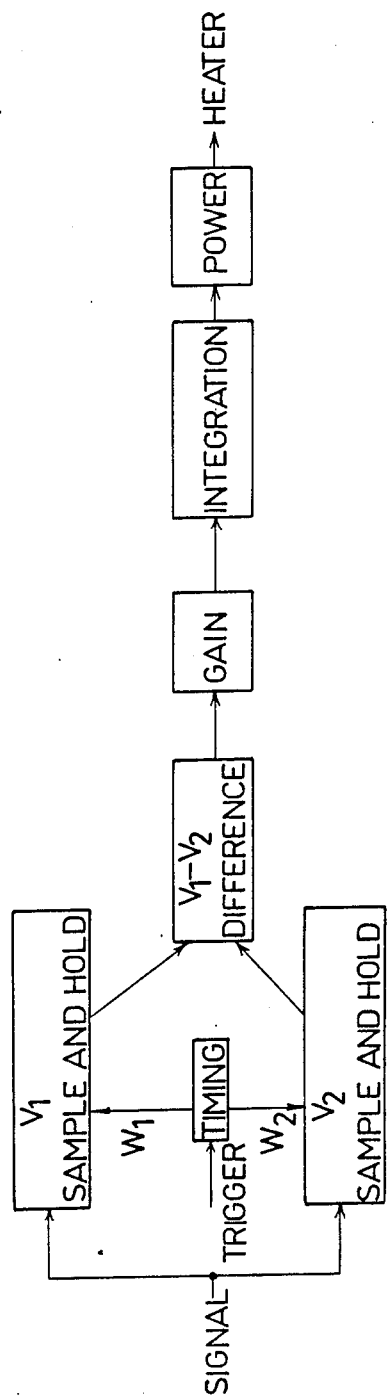
FIG. 4 is an electrical block diagram illustration of the electronic circuitry providing control of the apparatus of FIGS. 1 and 2.

FIG. 4 illustrates, in schematic form, the structure of the feedback control apparatus. This apparatus reads the average signal intensities $V_1$ and $V_2$ during the corresponding time intervals $W_1$ and $W_2$, by means of commercial sample and hold integrated chips. The difference $V_1-V_2$ is amplified and fed into an integration unit which operates an electrical power source which supplies electrical current to the heating element.

When the system is stabilized, the values $V_1$ and $V_2$ are equal and the input signal to the integration unit is zero, resulting in a constant heat supply from the heating element 57 and therefore constant temperature at the laser head. If the laser cools down as a result of any perturbation the absorption line moves rightward, causing the value $V_1$ to increase and the value $V_2$ to decrease. In this situation, the amplified signal difference $V_1-V_2$ charges the integration unit and results in an increase in the output current to the heating element 57. This extra heat increases the laser temperature by a small amount and causes the absorption line to return to its correct place.

If the laser increases in temperature for any reason, the absorption line moves leftward, causing a negative signal difference $V_1-V_2$ which discharges the integration unit and decreases the heating current. As a result the laser cools down and the absorption line shifts back to its correct place.

It will be appreciated by persons skilled in the art that the present invention is not limited by what has been particularly shown and described hereinabove. Rather the scope of the present invention is defined only by the claims which follow:

We claim:
1. Laser detection apparatus comprising:
   a laser having an active region and providing a double beam of coherent radiation;

a sample to be tested located in a first part of said double beam of coherent radiation;

a radiation detector arranged to receive radiation passing through the sample to be tested for providing an outut indication of absorbance;

a reference sample disposed in a second part of said double beam;

means for sensing absorption of the coherent radiation at the reference sample;

means for providing selectable heating of the active region of the laser; and means for providing a control signal to said selectable heating means in accordance with the sensed absorption of the coherent radiation at the reference sample.

said means for providing a control signal comprising means for determining the difference between the signal intensities of said coherent radiation at the leading and trailing slopes of an absorption line characteristic of said coherent radiation and means for causing said control signal to represent both the sign and the amplitude of said difference.

2. Apparatus according to claim 1 and wherein said means for providing selectable heating of the active region of the laser comprises a resistor.

3. Apparatus according to claim 1 and wherein said means for providing selectable heating of the active region comprises heating means located in a laser mounting.

4. Apparatus according to claim 1 and wherein said means for sensing absorption comprises means for determining the intensity of the coherent radiation at the peak and at the slopes of an absorption line thereof and means for providing an output signal in accordance with the difference between the sensed intensity at the peak and the average sensed intensity at the slopes.

* * * * *